United States Patent [19]

Liping

[11] Patent Number: 5,344,383

[45] Date of Patent: Sep. 6, 1994

[54] APPARATUS FOR RADIOACTIVE TREATMENT INSIDE THE HUMAN BODY AND THE METHOD USING THE SAME

[76] Inventor: Wang Liping, 209 Tiyuanbei-binshuixili No. 30, Hexi District, Tianjin, P.R., China

[21] Appl. No.: 929,222

[22] Filed: Aug. 14, 1992

[30] Foreign Application Priority Data

Aug. 17, 1991 [CN] China .............................. 91105575.4

[51] Int. Cl.$^5$ .............................................. A61N 5/00
[52] U.S. Cl. ............................................ 600/3; 600/7
[58] Field of Search ........................................ 600/1–8

[56] References Cited

U.S. PATENT DOCUMENTS

| | | | |
|---|---|---|---|
| 3,669,093 | 6/1972 | Sauerwein et al. | 600/7 |
| 4,631,415 | 12/1986 | Sauerwein et al. | 600/1 |
| 4,851,694 | 7/1989 | Rague et al. | 600/3 |
| 4,881,937 | 11/1989 | Van't Hooft et al. | 600/3 |
| 5,030,194 | 7/1991 | Van't Hooft et al. | 600/3 |
| 5,120,973 | 6/1992 | Rohe et al. | 600/3 |

Primary Examiner—Lee S. Cohen
Assistant Examiner—John P. Lacyk
Attorney, Agent, or Firm—Sughrue, Mion, Zinn, Macpeak & Seas

[57] ABSTRACT

An apparatus for radioactive treatment inside the human body mainly comprises a cable with a real source at its end, which passes through the annular grooves of two grooved reels, the guide hoses of a guide hose mechanism, and a storing case. The guide hose mechanism has two front guide hoses, two rear guide hoses and a three-forked connector. One of ends of two front guide hoses are connected with two branches of the three-forked connector and the other ends of the hoses are tangentially connected with the grooves of the grooved reels. One of ends of two rear guide hoses are tangentially with the grooves of the reels and the other ends converge at the storing case without connection. The grooved reels can be respectively driven to extend the front end or rear end to the human body to complete a treatment or sense the guide hose line.

5 Claims, 4 Drawing Sheets

APPARATUS FOR RADIOACTIVE TREATMENT INSIDE THE HUMAN BODY AND THE METHOD USING THE SAME

BACKGROUND OF THE INVENTION (1) Introduction

The present invention relates to an apparatus for radioactive treatment at the abnormal area (focus of a disease) inside the human body and the method using the same, and particularly to a apparatus for radioactive treatment with a new mechanical structure for transporting a radioactive source.

The apparatus have two independently driving reels with grooves, by which a cable with a radioactive source at its end is driven to transport the radioactive source into the abnormal area of the human body along a guide hose inserted in the human body in advance to carry out a radioactive treatment.

(2) Description of Prior Art

At present, the apparatus for treating a part of the human body with radioactive material has two driving rolls respectively with a helical groove on its periphery and two cables, one of which has a real source (radioactive material) at one of its ends and the other of which has a dummy (a nonradioactive materials has the same shape and size as the real one). The cables are wound around and driven by the rolls. The rotation of the rolls stretches or winds the cables so that the dummy or real source can be transported into the human body to carry out a treatment or determine the position of the abnormal area and condition of the guide tube line.

During the period of treatment, the cable with a dummy is first driven by a roll to transport the dummy to the abnormal area along the tube inserted in the human body to determine whether the hose is unblocked. Then, the dummy is moved back and another roll drives the other cable with a real source so that the real source is transported to the abnormal area to finish the treatment.

However, in this apparatus, the cables are respectively wound along the helical grooves of the rolls and the length of the helical groove limits the transporting distance of the real sourceδummy, which results in the limitation of the treatment to the abnormal area at the deep part of the human body. Further, the prior apparatus has another disadvantage of too many parts because of requirement of two cables to transport a real source and a dummy respectively.

Accordingly, the object of the invention is to provide an apparatus for radioactive treatment inside the human body, which comprises only one cable with a real source and has advantages of long distance of the extension of the cable and of conveniently changing the extending distance by using cables with various lengths.

SUMMARY OF THE INVENTION

According to the present invention, the apparatus for radioactive treatment inside the human body has only one cable. A radioactive source (i.e. real source or radioactive material) is arranged at the front end of the cable. The diameters at the front and rear ends of the cable correspond to that of the guide hoses through which the cable passes. The apparatus also has two grooved reels, each of which has an annular groove, two belts, and a plurality of the belt guiding rollers. The belts are guided by the rollers and respectively cover an arc length of the periphery of each grooved reels. The apparatus further has a guide hose mechanism which comprises two front guide hoses, two rear guide hoses and a three-forked connector. One branch of the three-forked connector is communicated with a guide hose connecting with the applicator inserted into the human body, and the other two branches are respectively connected with one of ends of the two front guide hoses. The other ends of two front guide hoses are respectively arranged at the annular grooves of the reels and tangentially contact with the wall of the groove. One of ends of two rear guide hoses are also arranged at the grooves of the reels while the other ends are converged in a storing case but not connected. The apparatus further has a shielding container. Two front guide hoses pass through the shielding container and the portions therein are bent to substantially Z-shaped. The apparatus further comprises a motor for driving the grooved reels, photoelectric coders and a photoelectric sensing switch.

During preparation before a treatment, the cable with a radioactive source is arranged through the guide hose mechanism and the annular grooves of the reels in such a manner that: the middle length of the cable is arranged in the storing case; the front length passes through a rear guide hose, along the groove of a reel tangentially connecting with above rear guide hose, and into a front guide hose tangentially connecting with the reel, and the front end is driven with a radioactive source by the motor to go away from a source storing container and stop at the shielding container, the rear length passes another rear guide hose, another reel, and another front guide hose in the same manner as above with the rear end stopping at the shielding container.

During treatment, firstly the applicator is inserted into the human body and connected with the three-forked connector by means of a guide hose. Secondly by means of the frictional force between the annular groove and the cable, the rear end of the cable passes through a front guide hose and the three-forked connector and enters the human body to determine whether the whole guide hose line is unblocked. Because a great length of the cable is stored at the storing case, the front end, i.e. the end with a radioactive source in the shielding container, has no movement during the movement of the rear end and only a certain length of the cable stored in the storing case is pulled out. By means of turning above grooved reel reversely, the rear end of the cable is pulled back to the original position and the certain length of cable returns to the storing case again. Then the other reel is driven and the front end of the cable with a radioactive source is transported to pass through the three-forked connector and enters the human body to carry out a treatment. Likewise, because only one grooved reel is driven this time and only the length of the cable stored in the storing case is stretched, the rear end of the cable has no movement. The apparatus can have a great of length of the cable stored in the storing case, by means of which the radioactive source can be transported a long distance. Further the apparatus has advantages of conveniently changing the radioactive source, conveniently sensing, exactly positioning and greatly depending.

Further objects and advantages of the invention will appear from the following description taken together with the accompanying drawings

DETAILED DESCRIPTION OF THE PREFERRED EMBODIMENTS

Figure 1:
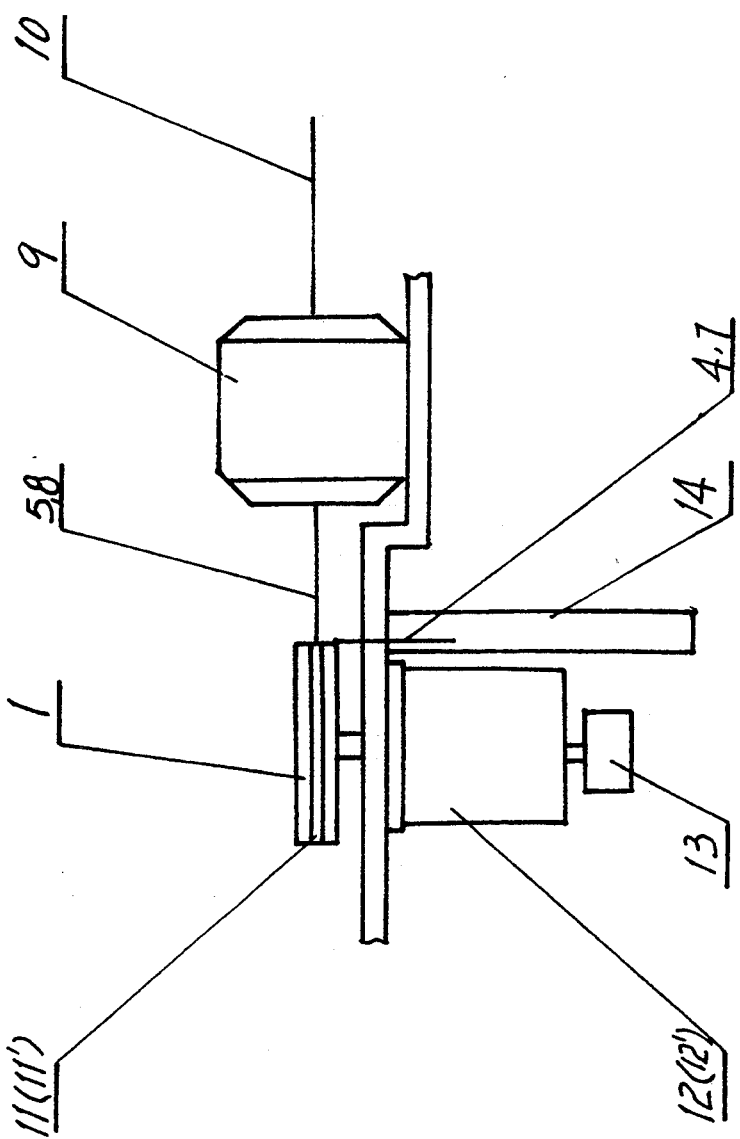
FIG. 1 is a schematic view of a guide hose mechanism for transporting a radioactive source.
Figure 2:
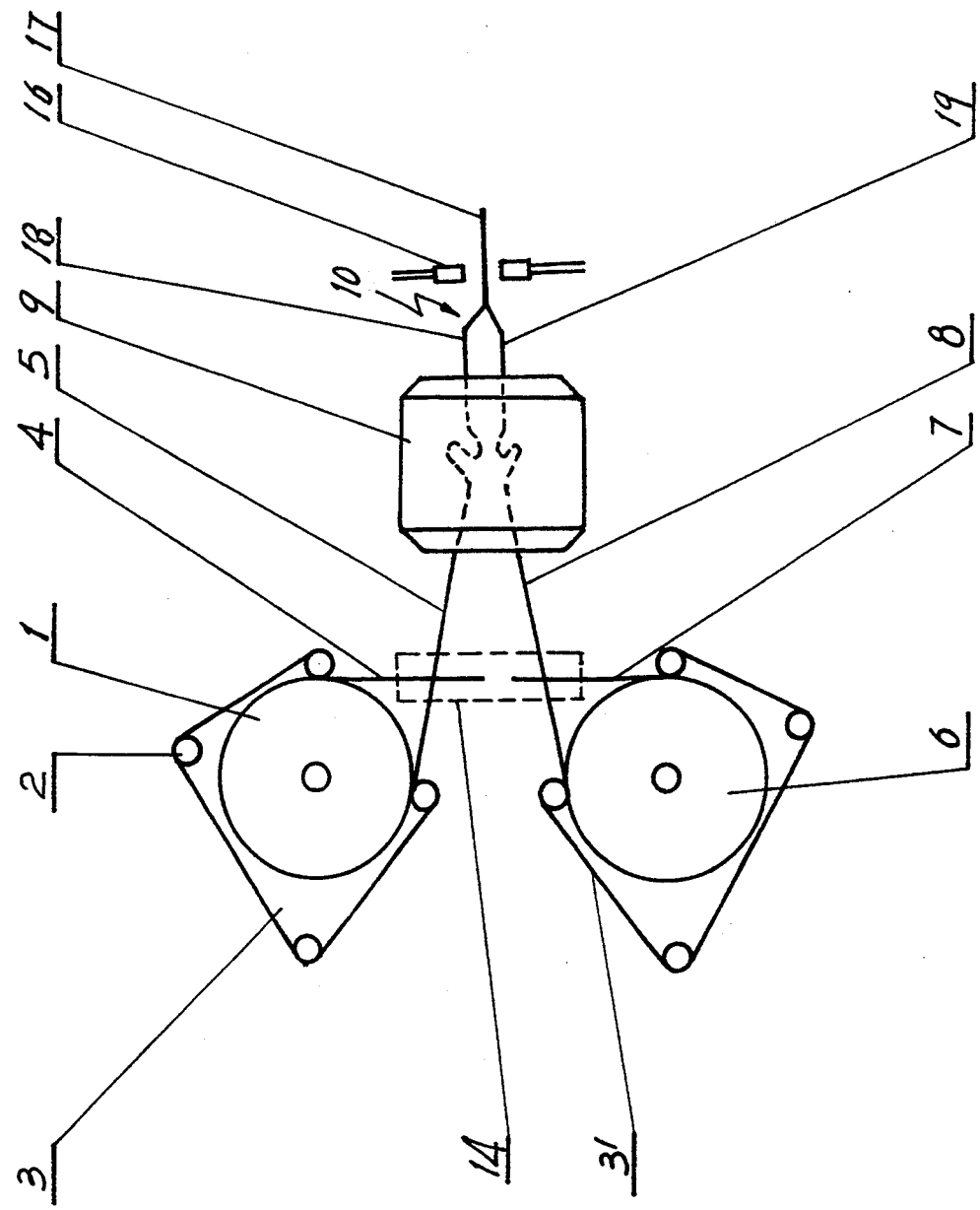
FIG. 2 is a schematic top view of the mechanism shown in FIG. 1.
Figure 3:
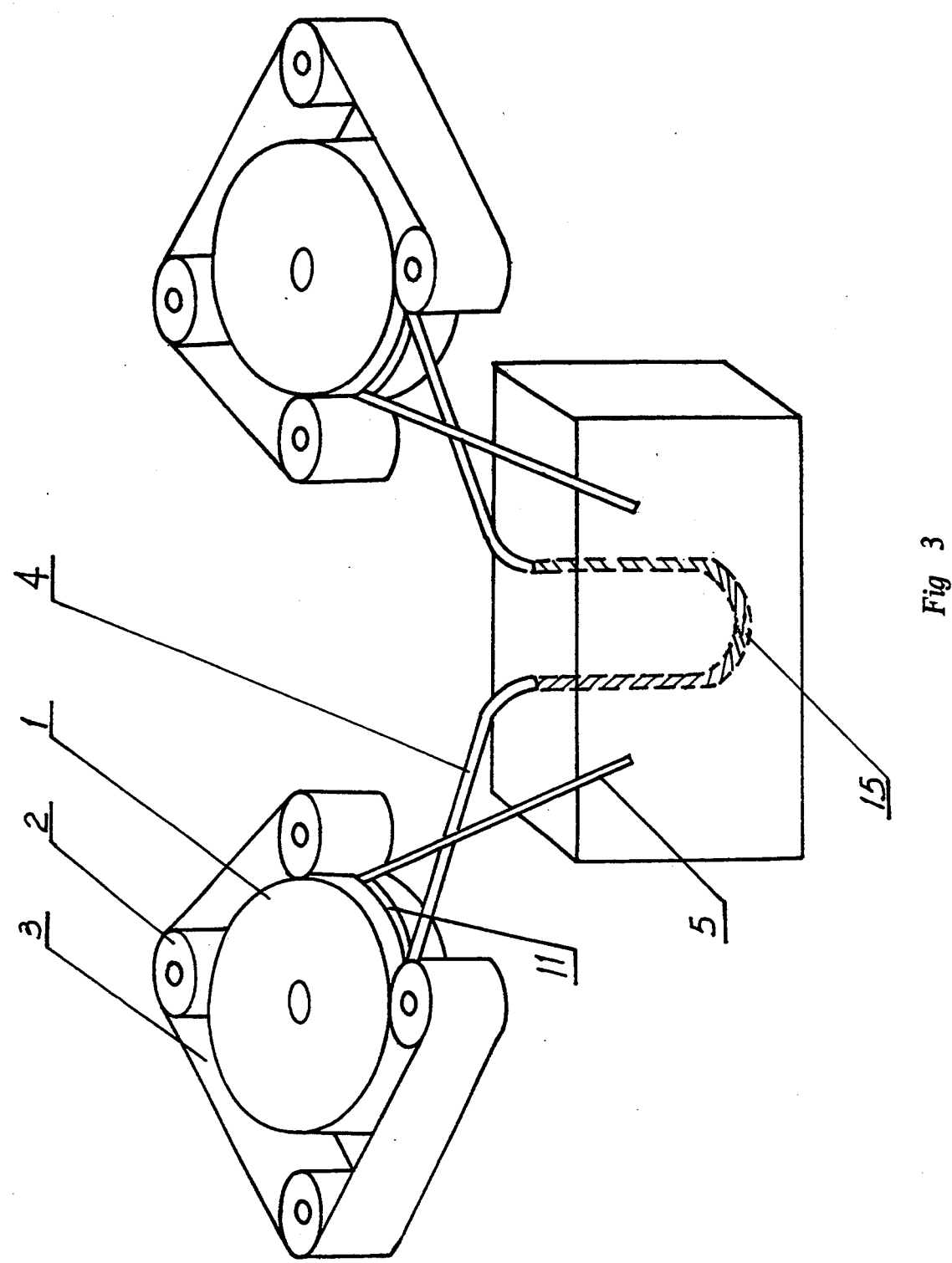
FIG. 3 is a schematic prospective view showing how a cable extends.

Reference is first made to FIGS. 1 and 2. The apparatus according to the first embodiment of the invention has a guide hose mechanism, two grooved reels 1 and 6, a shielding container 9, a photoelectric coder 13, storing case 14, a cable 15, two belts 3 and 3', belt guiding rollers 2 and a photoelectric sensing switch 16. The guide hose mechanism has two front guide hoses 5 and 8, two rear guide hoses 4 and 7, and a three-forked connector 10. The two grooved reels have the substantially same structure. For simplicity, only the structure and operation of the grooved reel 1 is described below in detail.

The grooved reel 1 has an annular groove 11 and is connected with the driving shaft of a motors 12 to be driven thereby as show in FIG. 1. The photoelectric coder 13 is connected with the other end of the shaft and used to sense the turning angle of the motor 12. The cable 15 with a radioactive source at its front end is wound in the annular groove 11 and a belt 3 guided by four rollers 2 tightly covers an arc length of the periphery of the grooved reel 1 to prevent the cable 15 there from coming away from groove 11. One of ends of the front guide hose 5 and the rear guide hose 4 are arranged to respectively tangentially connect with the annular groove 11 as shown in FIG. 2.

Likewise, the grooved reel 6 is driven by another motor 12' and the length of cable 15 in the groove 11' is covered by the belt 3'. The front and rear guide hoses 8,7 are provided with their ends tangentially connecting with the groove 11'.

The branch 17 of the three-forked connector 10 is connected with a guide hose which is used to be inserted into the human body and other branches 18,19 of the connector 10 are respectively communicated with the other ends of two front guide hoses 5, and 8 as shown in FIG. 2. The storing case 14 is provided, where a great length of the cable 15 is stored and one of ends of the rear guide hose 4 and 7 converge without connection.

As shown in FIG. 2, The shielding container 9 is provided between the three-forked connector 10 and the grooved reels 1 and 6. The portions of two front guide hose 5 and 8 passing through the shielding container 9 are bent to Z-shaped. The photoelectric sensing switch 16 is provided near the branch 17 of the connector 10 to sense the output of the radioactive source coming from the shielding container 9.

The cable 15 is arranged in the annular grooves 11, 11' of the reels 1 and 6, and extends through the guide hose mechanism with its front and rear ends both staying at the shielding container. The belt 3 tightly covers the length of cable 15 in the groove 11 between the points where the front and rear guide hoses 5, 4 is tangential with the groove. The belt 3' acts on the reel 6 in the same manner as above.

In practice, the front end of the cable 15 is at the front guide hose 5 and its rear end at the front guide hose 8. First the grooved reel 6 is driven by means of the shaft of the motor 12' and a certain length of the cable 15 in the storing case 14 is pull out under the frictional force of the cable 15 and the groove 11 to stretch the rear end of the cable to pass through the branch 17 to determine whether the guide hose line is unblocked. Then the grooved reel 6 is driven to turn reversely to pull the cable 15 back to the front guide hose 8 in such a manner that the certain length of the cable 15 is taken back to the storing case again. Under the condition of unblocked hose line, the reel 1 is driven to extend the front end of the cable 15 to pass through the three-forked connector in such a manner that a certain length of the cable 15 in the storing case is pulled out to transport the radioactive source to the human body without the movement of the rear end of the cable 15.

Figure 4:
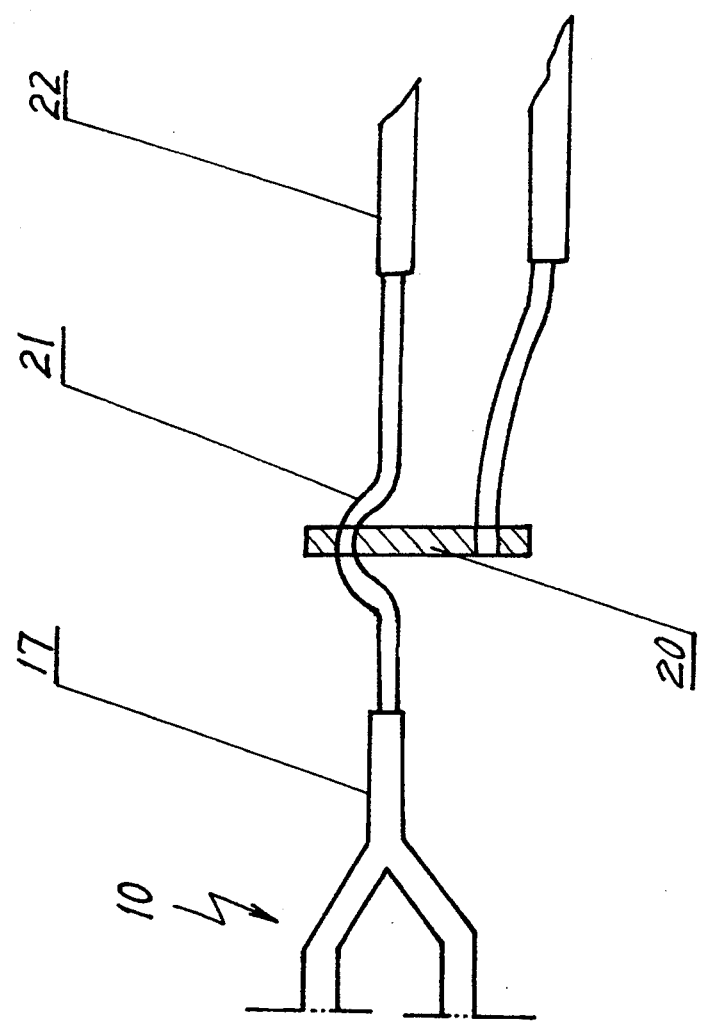
FIG. 4 is a schematic view showing the portion of the apparatus according to the second embodiment of the invention.

FIG. 4 shows the second embodiment of the invention which is different from the first one in that the branch 17 of the three-forked connector 10 is connected with a turnable rocking arm 19 which is turnable and coupled with a hose connecting disc 20. The hose connecting disc 20 has a plurality of axial through holes which are respectively communicated with connecting hoses 21 to connect applicators 22, whereby the source at the front end of the cable 15 can be transported through the holes of the hose connecting disc 21 to different applicators 22. Therefore in this embodiment a radioactive source can be transported into a human body through different applicators while in the first embodiment the source only can be transported into the human body through one applicators.

While the description of the invention has been given with respect to preferred embodiments, it is not to be considered in a limited sense. Variation and modification will occur to those skilled in the art. Reference is made to the appended claims for a definition of the invention.

What is claimed is:

1. An apparatus for radioactive treatment inside a human body, wherein, the apparatus comprises:

a cable having front and rear ends, a radioactive source being provided at said front end, and the diameters of said front and rear ends corresponding to those of two front and two rear guide hoses through which the cable passes;

two grooved reels, in which at the periphery of each a single annular groove is formed;

two belts, which are guided by guiding rollers and respectively cover an arc length of the periphery of each grooved reel;

a storing case; a guide hose mechanism, which comprises said two front guide hoses, said two rear guide hoses, and a three-forked connector; an applicator adapted to be inserted in said body; one branch of the connector being connected to a hose portion which is connected to said applicator, the other two branches of the connector respectively connecting with one of the ends of each of the front guide hoses, the other ends of each of the front guide hoses being tangentially arranged to connect with the grooves of the grooved reels, one of the ends of each of the rear guide hoses being tangentially arranged to connect with the grooves of the grooved reels and the other ends being converged in said storing case; a shielding container being arranged between the three-forked connector and the grooved reels, through which the front guide hoses pass; the cable extending along the grooves of the grooved reels and the guide hose mechanism, and a certain length of the cable being stored at the storing case.

2. An apparatus according to claim 1 wherein portions of the two front guide hoses in the shielding container are bent to the substantially same shape.

3. An apparatus according to claim 2 wherein said shape is substantially Z-shaped.

4. A method used to operate the apparatus claimed in claim 1, which comprises the following steps:
- (a) connecting one branch of the three-forked connector with the hose portion inserted into the human body;
- (b) driving one of the grooved reels to pull out a certain length of the cable in the storing case so that the rear end of the cable passes through the three-forked connector and enters the human body; reversely driving the one reel to pull the certain length of the cable into the storing case so that the rear end of the cable returns to the shielding container;
- (c) under the condition of unblocked guide hose line, driving the other reel to pull out a certain length in the storing case so that the front end with the radioactive source passes through the three-forked connector and enters the human body to carry out a treatment; after finishing the treatment, reversely driving the other reel to pull the certain length of cable into the storing case so that the front end of the cable returns to the shielding container.

5. The apparatus of claim 1 wherein said belts cover the whole length of the cable wound on the reels.

* * * * *